United States Patent
Anelli et al.

(10) Patent No.: US 8,835,685 B2
(45) Date of Patent: Sep. 16, 2014

(54) PROCESS FOR THE PREPARATION OF CONTRAST AGENTS

(75) Inventors: Pier Lucio Anelli, Milan (IT); Marino Brocchetta, Pavia (IT); Enrico Cappelletti, Seregno (IT); Ornella Gazzotti, Pianengo (IT)

(73) Assignee: Bracco Imaging S.p.A., Milan (IT)

( * ) Notice: Subject to any disclaimer, the term of this patent is extended or adjusted under 35 U.S.C. 154(b) by 88 days.

(21) Appl. No.: 13/805,306

(22) PCT Filed: Jul. 14, 2011

(86) PCT No.: PCT/EP2011/062052
§ 371 (c)(1),
(2), (4) Date: Jan. 24, 2013

(87) PCT Pub. No.: WO2012/007547
PCT Pub. Date: Jan. 19, 2012

(65) Prior Publication Data
US 2013/0131382 A1      May 23, 2013

(30) Foreign Application Priority Data

Jul. 15, 2010 (IT) .............. PD2010A0222

(51) Int. Cl.
*C07C 233/65* (2006.01)
*C07C 231/12* (2006.01)
*C07C 231/10* (2006.01)

(52) U.S. Cl.
CPC ............. *C07C 231/12* (2013.01); *C07C 231/10* (2013.01)

USPC .......................................................... 564/153

(58) Field of Classification Search
CPC .................................................... C07C 231/12
USPC .......................................................... 564/153
See application file for complete search history.

(56) References Cited

FOREIGN PATENT DOCUMENTS

WO      97/05097 A1      2/1997

OTHER PUBLICATIONS

Office Action for Russian application No. 2013106503, mail date May 14, 2013 (agent's letter explaining Office Action in English).
Anelli-Pier-etal, Smiles Rearrangement as a Tool for the Preparation of 5-[(2-Hydroxyacyl)amino]-2,4,6-triiodo-1,3-benzenedicarboxamides: Main Pathway and Side Reactions., Tetrahedron, Elsevier Science Publishers, Amsterdam, NL, vol. 53, No. 34, Aug. 25, 1997, pp. 11919-11928, XP004106051, ISSN: 0040-4020.
PCT international Search Report for PCT/EP2011/062052, mail date Aug. 3, 2011.
PCT Written Opinion for PCT/EP2011/062052, mail date Aug. 3, 2011.
Office Action for Chinese application No. 201180034752.4, mail date Feb. 21, 2014 (English translation).

*Primary Examiner* — Shailendra Kumar
(74) *Attorney, Agent, or Firm* — M. Caragh Noone

(57) ABSTRACT

The present invention relates to a process for the preparation of 5-[(2-hydroxyacyl)amino]-2,4,6-triiodo-1,3-benzendicarboxamidic derivatives comprising the Smiles rearrangement of a suitable precursor, by contact of an aqueous solution of this latter with an anion exchanger solid phase.

10 Claims, No Drawings

PROCESS FOR THE PREPARATION OF CONTRAST AGENTS

CROSS-REFERENCE TO RELATED APPLICATIONS

This application is the national stage application of corresponding international application number PCT/EP2011/062052 filed Jul. 14, 2011, which claims priority to and the benefit of Italian application no. PD2010A000222, filed Jul. 15, 2010, all of which are hereby incorporated by reference in their entirety.

TECHNICAL FIELD

The present invention relates in general to a process for the preparation of 5-[(2-hydroxyacyl)amino]-2,4,6-triiodo-1,3-benzendicarboxamidic derivatives, useful as contrast agents in diagnostic techniques.

BACKGROUND ART

Contrast agents or contrast media, are substances that can alter the way in which a region is analyzed in medical imaging. In particular, they are able to change the contrast of an organ, an injury, or any other surrounding structure, to make visible such details that otherwise would be difficult to detect or appreciate.

Contrast agents are primarily used in the radiological or in the nuclear magnetic resonance diagnostic fields. Depending on the field of application, these derivatives present structural features, such as, in the case of molecules useful as contrast agents for X-rays analysis, the presence of one or more atom with high atomic number (e.g. iodine or barium). Iopamidol (N,N'-bis[2-hydroxy-1-(hydroxymethyl)ethyl]-5-[(2S)(2-hydroxy-1-oxopropyl)amino]-2,4,6-triiodo-1,3-benzendicarboxamide) and Iomeprol (N,N'-bis(2,3-di-hydroxypropyl)-5-[(hydroxyacetyl)methylamino]-2,4,6-triiodo-1,3-benzendicarboxamide), whose structural formulas are indicated below, are two of the numerous tri-iodinated diagnostic agents, commercially available and widely used for this purpose:

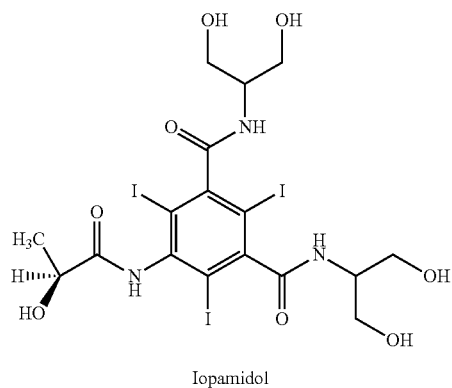

Iopamidol

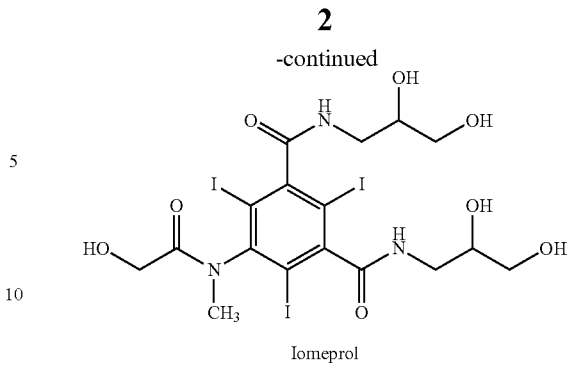

Iomeprol

Among the various synthetic procedures known in the art for the preparation of tri-iodinated aromatic derivatives useful in radiology applications, some of said procedures involve the rearrangement of an appropriate tri-iodo phenyl ether precursor to give the desired product, wherein a new amide functional group is obtained throughout a structural rearrangement of the corresponding ether group (such rearrangement is known as a "Smiles rearrangement", see as a general reference: S. Smiles et al., J. Chem. Soc 1931, 3264).

In particular, in this regard, WO97/05097 describes the preparation of iopamidol via Smiles rearrangement, starting from a given ether intermediate (this latter obtained by a $SN_2$ reaction of a precursor, in a salt form thereof) with a (R)-2-propanamidic derivative in various organic solvents, according to the following scheme:

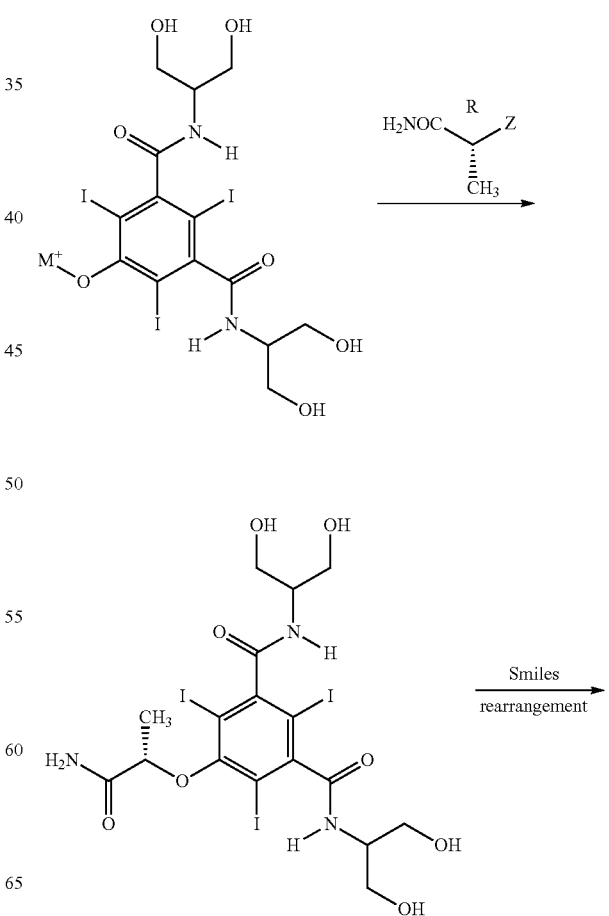

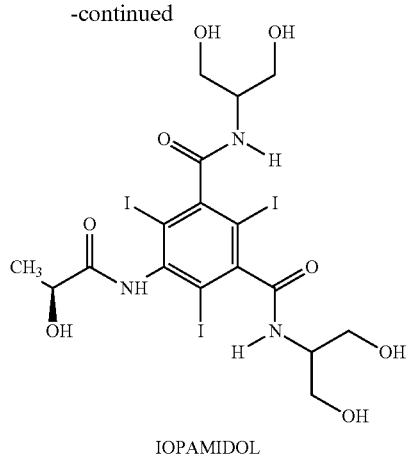

IOPAMIDOL

Said rearrangement is carried out in an alkaline alcohol mixture, typically constituted by methanol in the presence of KOH, at reflux for 2 hours, thus providing iopamidol with an overall yield of the two steps of 56%. Also exemplified in WO97/05097 are (R)-2-propanamidic derivatives in which the leaving group Z, involved in the first condensation step, is a leaving group generally chosen from: tosylate (TsO), mesylate (MsO) and chlorine.

Anelli et al. (Tetrahedron, Vol. 53, No. 34, 1997, pp 11919-11928) describe the preparation of 5-[(2-hydroxyacyl)amino]-2,3,6,-triiodo-1,3-benzendicarboxamidic derivatives, also including iomeprol and iopamidol, by Smiles rearrangement of a suitable ether precursor. In particular, there are described two methods (method A and B) comprising the use of a base, respectively in the presence of water or of an organic solvent, such as DMF. Both methods however lead to the co-formation of side products in varying amounts, due to the competitor reactions of cyclization and/or hydrolysis of the starting substrate. Also, the use of an aqueous solvent in the preparation of iopamidol results in a drastic reduction in the yield, compared to the same reaction when carried out in DMF (17.9% vs 99% of method A vs method B).

It should be noted, finally, that in the case of substances intended for a parenteral use as contrast agents, the final chemical and optical purity are of fundamental importance, as specifically required by the health authorities.

We have now found a new process for the preparation of 5-[(2-hydroxyacyl)amino]-2,4,6-triiodo-1,3-benzendicarboxamidic derivatives, such as iopamidol and iomeprol, via Smiles rearrangement of a suitable tri-iodine ether precursor, by contact of an aqueous solution of said precursor with an anion exchanger solid phase. The process of the present invention, comprising an aqueous solvent system, allows advantageously to carry out the reaction in more favourable conditions, even from the environmental point of view, than the prior art and, even more advantageously, it allows to obtain the final products, useful as contrast agents for example in radiology, with high yields, high degree of optical purity and substantially free of by-products.

SUMMARY OF THE INVENTION

The present invention relates to a process for the preparation of a 5-[(2-hydroxyacyl)amino]-2,4,6-triiodo derivative of general formula (5) or a pharmaceutically acceptable salt thereof:

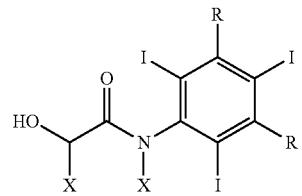

wherein:
R is independently in each occurrence a group selected from: —COOR' and —CON(R')$_2$;
R' is independently in each occurrence: hydrogen or a linear or branched (C$_1$-C$_4$) alkyl group, optionally substituted by one or more hydroxy groups as such or in a protected form thereof; and
X is hydrogen or a linear or branched (C$_1$-C$_4$) alkyl group;
by Smiles rearrangement of a compound of general formula (4) or a salt thereof:

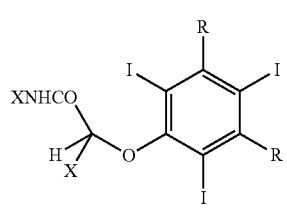

wherein:
R, R' and X are as defined above;
said rearrangement obtained by contacting compound (4) with an anion exchanger solid phase, in the presence of an aqueous solvent.

In more detail, the solid phase can be an anion exchanger resin suitably selected from those known in the art, such as a styrene or a polyamino acrylic core resin, variously functionalized, e.g. with quaternary ammonium groups, such as Amberlite® or equivalent, or Dowex® or equivalent types, or Purolite® type resin or equivalents, available in different meshes and porosities. Preferably, the resin is selected from: Amberlite® IRA400 (Chemical Abstract Number (CAS No.) 9002-24-8) and Purolite® A830 (Chemical Abstract Number (CAS No.) 457070-04-1).

Preferably, the chosen resin is suitably packaged in a column to allow the contact with the aqueous solution or suspension containing the precursor (4) typically by elution throughout the column.

In this regard, the aqueous solvent is preferably water.

In a preferred aspect of the invention, in the formulae (4) and (5) above:
R is a group selected from:

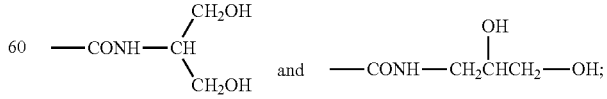

and X is independently methyl or hydrogen.

According to an even more preferred embodiment, the present process refers to the preparation of a compound of formula (5) wherein:

R is

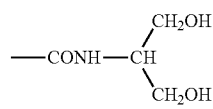

and X is hydrogen,
or wherein:
R is

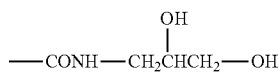

and X is methyl.

According to a further aspect, the present invention relates to a process for the preparation of (5), substantially as described above, wherein the compound of formula (4) is obtained by nucleophilic substitution of a compound of formula (2), or a salt thereof, with a nitrophenyl sulfonyl amide derivative of formula (3), in the presence of a solvent selected from: water and aqueous mixture with one or more polar organic solvent:

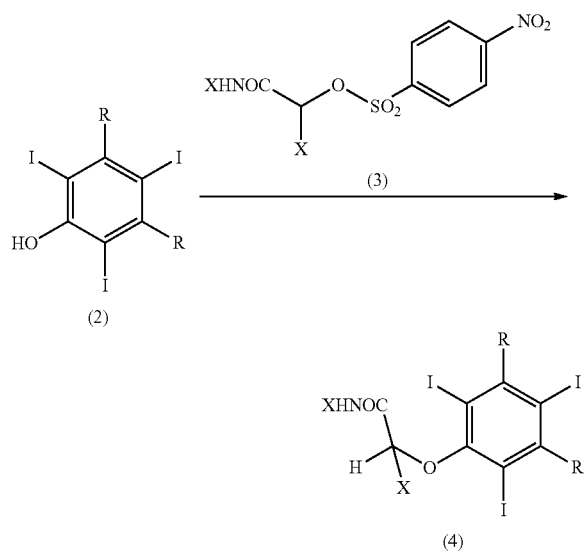

wherein:
R is independently in each occurrence a group selected from:
—COOR' and —CON(R')$_2$;
R' is independently in each occurrence: hydrogen or a linear or branched ($C_1$-$C_4$) alkyl group, optionally substituted by one or more hydroxy group as such or in a protected form thereof; and
X is hydrogen or a linear or branched ($C_1$-$C_4$) alkyl group.

Preferably the compound of formula (2) is in the form of a salt, typically an alkaline salt, preferably sodium salt.

According to a further preferred embodiment, the compound of formula (3) is selected from:
(R)-2-[[(4-nitrophenyl)sulfonyl]oxy]propylamide; and
2-[[(4-nitrophenyl)sulfonyl]oxy]ethylamide,
whereas the compound of formula (5) is preferably iopamidol or iomeprol. Advantageously, the process of the present invention allows to isolate the final product (5) iopamidol, with yields and optical purity higher than the prior art (as described for example in WO97/05097).

DETAILED DESCRIPTION OF THE INVENTION

The present invention relates, in general, to a process for the preparation of 5-[(2-hydroxyacyl)amino]-2,4,6-triiodo derivatives through a Smiles rearrangement reaction, by contacting a precursor of formula (4), or a salt thereof, with a suitable anion exchanger solid phase.

Unless otherwise specified, the term "linear or branched ($C_1$-$C_4$) alkyl group" means a linear or branched alkyl group having 1 to 4 carbon atoms, such as for example: methyl, ethyl, propyl, iso-propyl, butyl, isobutyl and the like, preferably methyl.

The term "anion exchanger solid phase" or "anion exchanger" or "solid phase" means a solid support able to perform an exchange of anions with the solution or suspension in contact thereto.

According to a general embodiment, and as described in more detail in the experimental part, the compound of formula (4), optionally obtained by reaction of the compound of formula (2) with the appropriate amide derivative of formula (3), is contacted with a suitable solid phase, leading to the selective formation of the final compound (5) with high yields and substantially free of side products.

Said contact may be obtained by elution through a column packed with the proper solid phase, or alternatively, by a so called "batch method". This latter is intended as any method that includes a suitable reactor in which the reagents involved in the process are brought into contact and reacted with each other, typically, under stirring.

According to a preferred embodiment, the contact between compound (4) and the solid phase is achieved throughout the column, and in this regard, the solid phase can be used as such and packed in a column in the moment of need, or alternatively, the solid phase can be present in an already pre-packed column, readily available on the market. As afore mentioned, the precursor (4), present in an aqueous medium, is contacted with the solid phase by elution throughout the column, or by vigorous stirring in the case of a batch method, at a given rate of elution or stirring, respectively, and for an appropriate period of time, generally varying from a few hours to several days, mainly depending on the amount of the starting material. In the case of a column process, the compound (4), is usually eluted in an aqueous medium several times throughout the column, according to known methods, such as for example, the gravity method or the high pressure method at a constant flow rate, e.g. about 600-800 mL/sec.

According to a preferred aspect, the compound (4) is dissolved or suspended in an aqueous medium selected from: water and aqueous mixtures of a polar organic solvent, for example an alcohol such as methanol, ethanol or the like, or a polar ether such as dioxane, tetrahydrofuran or similar. Preferably, the compound (4) is dissolved or suspended in water.

Typically, and in accordance with a preferred embodiment, the solid phase is a strong anion exchanger resin or a weak anion exchanger resin, both commercially available and preferably having a styrene-divinylbenzene core. Examples of such suitable resins are: Amberlite® (available from Rohm and Haas Company, Philadelphia, USA), Dowex® or Purolite® (available from The Purolite Company, Bala Cynwyd, Pa., USA). In more detail, preferred resins are: Purolite® A-830 (CAS No. 457070-04-1) and Amberlite® IRA 400 (CAS No. 9002-24-8), being this latter even more preferred.

The selected resin can be variously functionalized or used as such, or even further, the resin can be previously activated by methods known to the expert in art, such as, acid washing activation, for instance with hydrochloric acid.

It has to be noted that the strength of the anion exchanger, the contact times and the temperature should be selected in order to maximize the yield of the desired final product, with particular regard to an industrial scale application of the present process. It was noted in fact that under the reaction conditions of this process, the use of a weak anion resin can lead to the final product with particular predilection to the obtainable high degree of purity. On the other hand, the use of a strong anion resin can be convenient in those cases where the effectiveness of the Smiles rearrangement, in terms of yield, is preferred.

In accordance with the present invention, the Smiles rearrangement to give the derivatives of formula (5) is carried out by choosing the appropriate anion exchanger resin, at a pH of the reaction comprised from about 6 to about 9, preferably from about 6 to about 7, for a reaction time ranging from 24 to 40 hours, and typically operating at room temperature, e.g. at a temperature of about 15-30° C. Even more preferably, the present process describes the preparation of (5) by contacting a solution of the corresponding precursor (4) in water, at a molar concentration from about 0.05 to 0.07 M, by elution throughout a column packed with Amberlite®IRA-400 resin, and operating at a pH from about 6 to about 7 (molar concentrations of a given substance is herein intended as the molar amount of such substance, divided for the total mixture volume).

During the column process, in order to maintain the pH as constant as possible, it is recommended to evaporate potential amine residuals (as generally released by the resin) from the eluted solution. This expedient allows, conveniently, to obtain a final product in very high yields, even up to about 90%. In this case, the solution thus remaining after such partial evaporation, and in case, containing part of the starting compound (4) not yet reacted, is diluted with water, or with the aqueous solvent used for the elution throughout the column, and re-eluted through the column. These last steps (i.e. evaporation and re-elution in the column) are preferably repeated one or more times, for example at regular intervals of 6 and 24 hours, during the whole process, in order to obtain the final product in high yield, as described in the attached experimental part.

The detection of the final compound (5) in the eluted solution, can be done by any analytical techniques known in the art, such as for example UV detection or the like.

The resin at the end of the process can be conveniently regenerated according to known techniques, such as for example, by washing it with a lower alcohol, e.g. methanol, thus conveniently allowing the reuse of the same resin in subsequent applications.

As extensively herein reported, the process of the present invention allows, advantageously, the preparation and isolation of compounds of formula (5), such as iopamidol and iomeprol, with high reaction yields (more than 90%), and final optical purity (enantiomeric excess "ee" 99%), operating in the presence of an aqueous solvent.

It will be recognized that, since the Smiles rearrangement in accordance with the present invention, occurs with retention of configuration, when X is other than hydrogen, the configuration of this stereocentre in (4) will be retained in the final product (5). Thus, in support of that, and by way of example, by the present process, it is possible to prepare iopamidol, i.e. (N,N'-bis[2-hydroxy-1-(hydroxymethyl) ethyl]-5-[(2S)-(2-hydroxy-1-oxopropyl)amino]-2,4,6-tri- iodo-1,3-benzendicarboxamide) as well as the corresponding (2R) isomer, starting from the corresponding precursor (4) in the (S) or (R) configuration, respectively. According to a preferred embodiment, the invention relates to the Smiles reaction leading to the formation of iopamidol.

In a further aspect, the present invention relates to a process for the preparation of (5) as previously described, characterised in that the compound of formula (4) is obtained by reaction of a compound of formula (2), or a salt thereof, with a nitrophenyl sulfonyl amide derivative of formula (3):

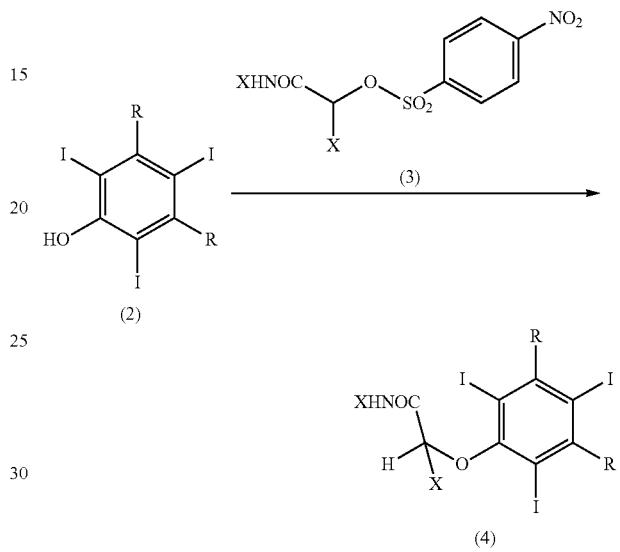

wherein:
R is independently in each occurrence selected from the group consisting of: —COOR' and —CON(R')$_2$;
R' is independently in each occurrence: hydrogen or a linear or branched (C$_1$-C$_4$) alkyl group, optionally substituted by one or more hydroxy group, as such or in a protected form thereof; and
X is hydrogen or a linear or branched (C$_1$-C$_4$) alkyl group;
in the presence of a solvent selected from: water and aqueous mixture with one or more polar organic solvent.

Preferably the starting compound of formula (2) is in the form of a salt thereof, typically an alkaline salt, preferably a sodium salt.

According to the preferred embodiments as above described, the compound of formula (3) is preferably selected from:
(R)-2-[[(4-nitrophenyl)sulfonyl)]oxy]propylamide and 2-[[(4-nitrophenyl) sulfonyl)]oxy]ethylamide.

According to the process for the preparation of (4) from (2) as described above, the final product (5) is advantageously obtained with yields higher than the prior art (82% vs. 56% as described for example in WO97/05097) and optical purity (ee) of more than 99%.

The nitrophenyl sulfonyl amide derivative of formula (3) can be conveniently prepared by methods known in the art (see e.g. Markert et al., Chem. Ber., 1927, 60, 2456) or, alternatively, purchased as such. Generally, the starting compound of formula (2) is present as a salt thereof, preferably as a sodium salt, whereas the pH of the reaction is maintained from 6 to 9. Preferably, said pH is from about 7 and about 8.

For the measurement of pH it is typically used a glass electrode, while the pH values can be changed, using a base, such as an inorganic base, for example, NaOH.

According to an illustrative embodiment of the invention and in accordance with the following experimental part, the compound (3) is added to the sodium salt of the compound (2), in an aqueous solvent selected from water or water mixed with a polar organic solvent, e.g. dioxane, tetrahydrofuran and the like, in a 1:1 ratio or preferably in the presence of an excess of water. In this respect, the selected polar organic solvent is dioxane and the weight ratio water/organic solvent is 2:1, or more preferably 3:1. According to a further preferred embodiment the aqueous solvent is a mixture of water/dioxane 3:1 by weight.

The reaction mixture is stirred at room temperature or, more preferably warmed up for instance at a temperature from about 50° C. to about 90° C., more preferably between 70° C. and 80° C. The pH of the reaction environment is monitored and possibly adjusted to have values from about 7 to about 8, as previously described. By monitoring the progress of the reaction, e.g. by TLC analysis, when the percentage of residual (2) turns out to be negligible (generally less than about 10%), the solution is thus worked up by purification and evaporation of the solvent in order to obtain the desired derivative (4).

The compound of formula (4) thus obtained is then subjected to Smiles rearrangement by the contact with an anion exchanger solid phase in the presence of an aqueous solvent, as extensively illustrated above. The final product (5) is hence obtained from (2) with yields higher than 70% (overall yield of two steps: 82%) and high optical purity (ee 99.5%) using a reliable process that allows working in the presence of aqueous reaction solvents.

It will be recognized in the present invention that when X is other than hydrogen, the compound (3), and consequently the compounds (4) and (5), have a chiral centre and, therefore, may be present in two configurations (R) or (S), otherwise called (D) or (L), as well as in a racemic form. We report the process that involves rearrangement of Smiles of a compound of formula (4) obtained by reaction of the appropriate precursor with (3), being this latter intended in either the configuration (R) or (S), leading to the formation of the final (5) in a stereospecific manner. Thus, for example, the present process can lead to the formation of the compound (N,N'-bis-[2-hydroxy-1-(hydroxymethyl)ethyl]-5-[(2-hydroxy-1-osso-propil)amino]-2,4,6-triiodo-1,3-benzendicarboxamide) having (2S) configuration (namely iopamidol) or the corresponding (2R) isomer, starting from the precursor (2-[[(4-nitrophenyl)sulfonyl)]oxy]propylamide (3) with configuration (R) or (S), accordingly. In fact, since the SN$_2$ type reaction between (3) and (2), the compound (4) is obtained by inversion of configuration. Conveniently, the subsequent Smiles reaction, occurring with retention of configuration, makes the whole process highly stereospecific.

Therefore, as widely reported above, the present invention allows for 5-[(2-hydroxyacyl)amino]-2,4,6-triiodo derivatives of general formula (5), useful as contrast agents in diagnostic imaging methods, with high yields and degree of optical purity, using a reliable and reproducible process, also applicable on an industrial scale, which comprises the Smiles rearrangement on an anion exchanger solid phase in the presence of an aqueous medium. This invention can be conveniently intended for the preparation of iopamidol or iomeprol, substantially free of by products, and in line with the purity specifications required for their use as contrast agents, typically in radiology.

The present invention will be now illustrated with examples that are not intended to pose any limitation to its scope.

EXPERIMENTAL PART

Example 1

Preparation of (5) Via Smiles Rearrangement in the Presence of an Anion Exchanger Solid Phase, in an Aqueous Medium (General Procedure)

A solution having a pH of 6-7 of the compound (4) in an appropriate aqueous solvent was loaded into a column packed with an anion exchanger solid phase, and eluted through the column at a constant flow. At intervals of 6 and 24 hours, the elution was stopped and the thus eluted solution, which showed a pH from about 9 to about 11, was partially evaporated and diluted with the aqueous reaction solvent, setting the pH to its initial value, by addition of a base. The reaction was continuously monitored, and the HPLC analysis showed a progressive decrease of the compound (4) in favour of (5).

Example 1a

Preparation of Iopamidol Via Smiles Rearrangement in the Presence of Amberlite® IRA400

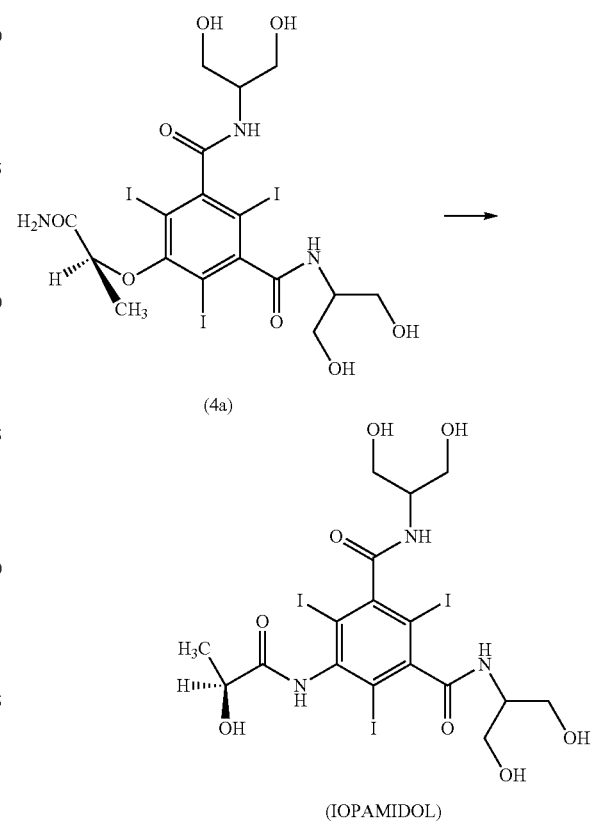

The general procedure of the Example 1 was repeated, using the compound of formula (4a) (7.5 g, 9.6 mmol) in H$_2$O (150 mL) in the presence of Amberlite® IRA-400, being this latter packed into a column. The elution time was 32 hours at a constant flow rate of 600 mL/hour. The HPLC analysis of the reaction showed that the concentration of (4a) decreases over the time in favour of iopamidol (93% yield, ee>99%) substantially without the concomitant formation of undesired by-products.

Example 2

Preparation of (4a) by reaction of (2a) with (R)-2-[[(4-nitrophenyl) sulfonyl)]oxy]propanamide

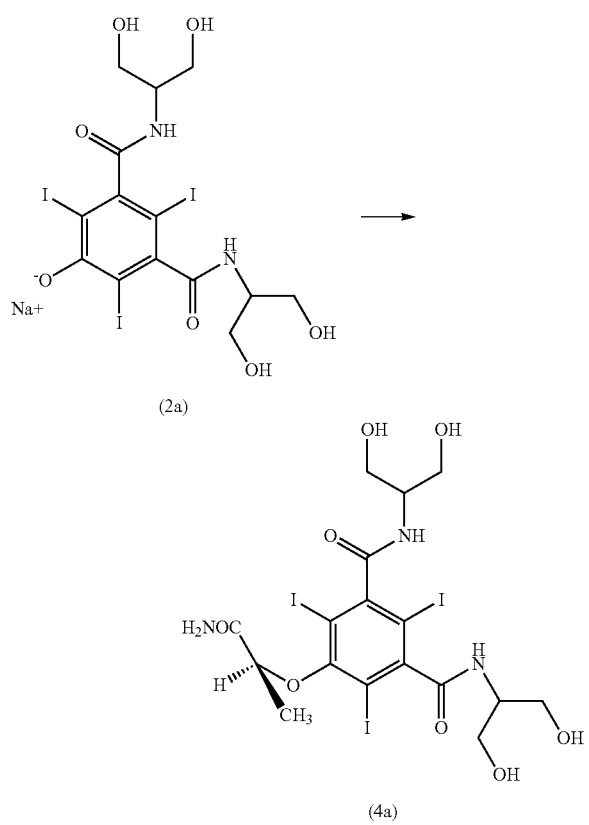

(R)-2-[[(4-nitrophenyl)sulfonyl)]oxy]propanamide (26.7 g, 97.2 mmol) was added portion wise over about 1.5 hours to a solution of 5-hydroxy-N,N'-bis[2-hydroxy-1-(hydroxymethyl)ethyl]-2,4,6-triiodo-1,3-benzendicarboxamide (2a) in the form of sodium salt (44.2, 60.8 mmol) in a solution of $H_2O$/1,4-dioxane 75:25 (about 300 mL), and the reaction mixture was stirred at 70-80° C. in the presence of a glass electrode for the pH measurement.

The pH of the reaction was maintained at about 7-8 by adding NaOH 1M, until the residual percentage of (2) was less than about 10%, as measured by TLC analysis.

The solution was concentrated and eluted through a column of Amberlite® IR-120, the eluate was neutralized with NaOH 2M (30 mL), concentrated under vacuum, and maintained at low temperature (about 5° C.) for 15 hours. After filtration and drying, a first batch of compound (4a) (33.3 g, 42.8 mmol, yield=71%) was obtained as a white solid.

The filtrate was further evaporated, the solid residue thus obtained was heated in ethanol, and the resulting suspension was filtered off to remove the insoluble sodium 4-nitrobenzensolfonate. After 15 hours at about 5° C., the second batch of compound (4a) thus obtained as crude was dissolved in water and purified by elution through a column of Amberlite® IR-120, eluting with water. The neutralized eluate was evaporated, and the solid residue was crystallized from ethanol to give the second batch of compound (4a) as a pure solid (6.9 g, 8.8 mmol, yield=15%) that was combined with the first batch, giving the compound (4a) with a total yield of 86%.

Example 3

Preparation of Iopamidol, from (4a) Prepared in Accordance with the Procedure of Example 2

The compound of formula (4a), obtained with the procedure of Example 2, was subjected to a Smiles rearrangement, according to the general procedure of the Example 1.

The final product was crystallized from ethanol to give the title compound with a yield of 95%.

Overall yield from (2) (Example 2+Example 3)=82%, HPLC 99.9%, $[\square]^{20}_{436}$=+144.3 (c 2.5 Cu (II) L2, $H_2O$)=99.5% over the theoretical value of 145.

The invention claimed is:

1. A process for the preparation of a 5-[(2-hydroxyacyl)amino]-2,4,6-triiodo derivative of general formula (5) or a pharmaceutically acceptable salt thereof:

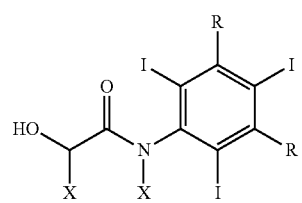

wherein:
R is independently in each occurrence a group selected from: —COOR' and —CON(R')$_2$;
R' is independently in each occurrence: hydrogen or a linear or branched ($C_1$-$C_4$) alkyl group, optionally substituted by one or more hydroxy groups as such or in a protected form thereof; and
X is hydrogen or a linear or branched ($C_1$-$C_4$) alkyl group;
by Smiles rearrangement of a compound of general formula (4) or a salt thereof:

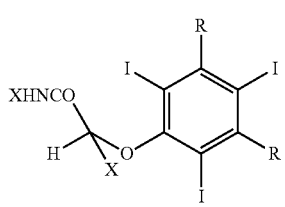

wherein:
R, R' and X are as defined above;
said rearrangement obtained by contacting compound (4) with an anion exchanger solid phase, in the presence of an aqueous solvent.

2. The process according to claim 1, wherein:
R is

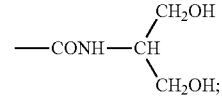

and
X is hydrogen.

3. The process according to claim 1, wherein:
R is

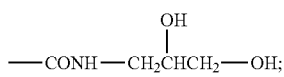

and

X is a methyl group.

4. The process according to claim 1, wherein the anion exchanger solid phase is a weak anion exchanger resin or a strong anion exchanger resin.

5. The process according to claim 4, wherein the anion exchanger solid phase is selected from: Amberlite® IRA 400 and Purolite® A830.

6. The process according to claim 1, wherein the aqueous solvent is water.

7. The process according to claim 1, wherein said rearrangement is carried out at a pH of 6 to 9.

8. The process according to claim 1, wherein the preparation of the compound of formula (4) is carried out by nucleophilic substitution of a compound of formula (2), or a salt thereof, with an amidic nitro phenyl sulfonyl derivative of formula (3),

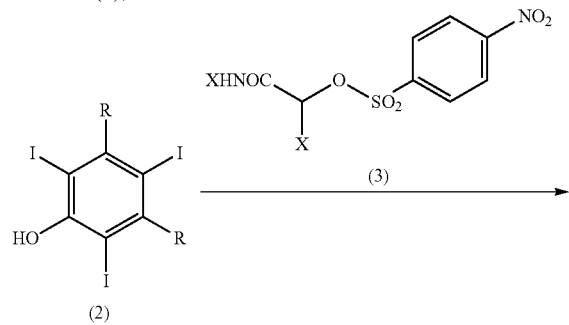

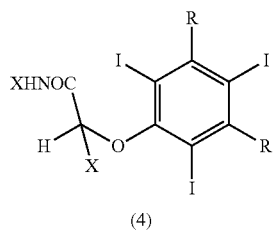

wherein:

R is independently a group selected from: —COOR' and —CON(R')$_2$;

R' is independently hydrogen or a branched or linear (C$_1$-C$_4$)alkyl group, optionally substituted with one or more hydroxy group, optionally in a protected form; and X is hydrogen or a branched or linear (C$_1$-C$_4$)alkyl group;

in the presence of a solvent selected from: water and a mixture of water with one or more organic polar solvents.

9. The process according to claim 8, wherein the compound of formula (3) is:

(R)-2-[[(4-nitrophenyl)sulfonyl)]oxy]propanamide; or

2-[[(4-nitrophenyl)sulfonyl)]oxy]ethanamide.

10. The process according to any one of claim 8 or 9, wherein the solvent is a mixture of water/dioxane in a ratio of 3:1 by weight.

* * * * *